United States Patent
Vyavahare et al.

(10) Patent No.: US 9,795,573 B2
(45) Date of Patent: Oct. 24, 2017

(54) MULTI-STEP CONNECTIVE TISSUE STABILIZATION METHOD AND STABILIZED TISSUE FORMED THEREBY

(71) Applicant: Clemson University, Clemson, SC (US)

(72) Inventors: Naren Vyavahare, Greenville, SC (US); Hobey Tam, Seneca, SC (US)

(73) Assignee: Clemson University, Clemson, SC (US)

( * ) Notice: Subject to any disclaimer, the term of this patent is extended or adjusted under 35 U.S.C. 154(b) by 186 days.

(21) Appl. No.: 14/495,067

(22) Filed: Sep. 24, 2014

(65) Prior Publication Data

US 2015/0087611 A1 Mar. 26, 2015

Related U.S. Application Data

(60) Provisional application No. 61/881,611, filed on Sep. 24, 2013.

(51) Int. Cl.
| | |
|---|---|
| *A01N 43/04* | (2006.01) |
| *A61K 31/70* | (2006.01) |
| *C12N 5/00* | (2006.01) |
| *C12N 5/02* | (2006.01) |
| *A61K 31/15* | (2006.01) |
| *A61K 31/7036* | (2006.01) |
| *A61K 35/34* | (2015.01) |
| *A01N 1/02* | (2006.01) |
| *A61K 45/06* | (2006.01) |
| *A61K 31/17* | (2006.01) |
| *A61K 31/7028* | (2006.01) |

(52) U.S. Cl.
CPC ............ *A61K 31/15* (2013.01); *A01N 1/0231* (2013.01); *A61K 31/17* (2013.01); *A61K 31/7028* (2013.01); *A61K 31/7036* (2013.01); *A61K 35/34* (2013.01); *A61K 45/06* (2013.01)

(58) Field of Classification Search
CPC .. A01N 1/0231; A61K 31/15; A61K 31/7036; A61K 35/34
See application file for complete search history.

(56) References Cited

U.S. PATENT DOCUMENTS

| | | |
|---|---|---|
| 3,918,455 A | 11/1975 | Coplan |
| 3,997,396 A | 12/1976 | Delente |
| 4,027,676 A | 6/1977 | Mattei |
| 5,123,912 A | 6/1992 | Kaplan et al. |
| 5,162,225 A | 11/1992 | Sager et al. |
| 5,200,248 A | 4/1993 | Thompson et al. |
| 5,242,644 A | 9/1993 | Thompson et al. |
| 5,263,984 A | 11/1993 | Li et al. |
| 5,268,229 A | 12/1993 | Phillips et al. |
| 5,496,627 A | 3/1996 | Bagrodia et al. |
| 5,512,600 A | 4/1996 | Mikos |
| 5,518,680 A | 5/1996 | Cima et al. |
| 5,611,981 A | 3/1997 | Phillips et al. |
| 5,716,404 A | 2/1998 | Vacanti et al. |
| 5,723,159 A | 3/1998 | Phillips et al. |
| 5,759,830 A | 6/1998 | Vacanti et al. |
| 5,770,193 A | 6/1998 | Vacanti et al. |
| 5,804,318 A | 9/1998 | Pinchuk et al. |
| 5,906,828 A | 5/1999 | Cima et al. |
| 5,942,436 A | 8/1999 | Dunn et al. |
| 5,972,505 A | 10/1999 | Phillips et al. |
| 6,303,136 B1 | 10/2001 | Li et al. |
| 6,306,424 B1 | 10/2001 | Vyakarnam et al. |
| 6,333,029 B1 | 12/2001 | Vyakarnam et al. |
| 6,365,149 B2 * | 4/2002 | Vyakarnam ......... A61F 2/30756 424/424 |
| 6,368,859 B1 | 4/2002 | Atala |
| 6,391,538 B1 | 5/2002 | Vyavahare et al. |
| 6,468,649 B1 | 10/2002 | Zhong |
| 6,521,431 B1 | 2/2003 | Kiser et al. |
| 6,544,548 B1 | 4/2003 | Siller-Jackson et al. |
| 6,753,311 B2 | 6/2004 | Fertala et al. |
| 6,790,455 B2 | 9/2004 | Chu et al. |
| 6,858,222 B2 | 2/2005 | Nelson et al. |
| 6,861,142 B1 | 3/2005 | Wilkie et al. |
| 6,861,211 B2 | 3/2005 | Levy et al. |
| 7,056,580 B2 | 6/2006 | Dugan |
| 7,374,673 B2 | 5/2008 | Marcus |

(Continued)

OTHER PUBLICATIONS

Conroy, et al., "Lubricious coatings for medical devices", dds&s, vol. 3, No. 4, pp. 89-92, (2004).
Harris, et al., "Assessment of the cytocompatibility of different coated titanium surfaces to fibroblasts and osteoblasts", Cytocompatibility of Titanium Surfaces, pp. 13-20 (2004).
Park; Joon Bu, Biomaterials: An introduction, pp. 230-231, 1992.
Ratner. et al, Biomaterials Science, An Introduction to Materials in Medicine, pp. 170-173, 1996.
"Bioerodible Hydrogels Based, on Photopolymerized Poly(ethylene glycol)-co-poly(a-hydroxy acid) Diacrylate Macromers,"by A.S. Sawhney, C.P, Pathak, and J.A. Hubbell: Macromolecules 1993, 26, American Chemical Society, pp, 581-587.

(Continued)

Primary Examiner — Lawrence E Crane
(74) Attorney, Agent, or Firm — Dority & Manning, PA

(57) ABSTRACT

A multi-step stabilization method for connective tissue is described. Stabilized tissues can exhibit increased resistance to degradation due to enzyme activity, fatigue and storage. The multi-step method includes a first step during which the tissue can be incubated with a glycosaminoglycanase inhibitor such as a sulfated oligosaccharide, one example of which being neomycin, a second step during which the tissue can be incubated with a crosslink activator such as a carbodiimide crosslink activator and/or a crosslinking agent such as a heterobifunctional crosslinking agent and/or a phenolic compound such as a tannin, examples of which include tannic acid and pentagalloylglucose, and a third step during which the tissue can be incubated with a second crosslink activator that can be the same or different as the first crosslink activator.

18 Claims, 4 Drawing Sheets

(56) References Cited

U.S. PATENT DOCUMENTS

| | | |
|---|---|---|
| 7,479,164 B2 | 1/2009 | Girardot et al. |
| 7,713,543 B2 | 5/2010 | Vyavahare et al. |
| 7,918,899 B2 | 4/2011 | Girardot et al. |
| 2001/0033857 A1 | 10/2001 | Vyakarnam et al. |
| 2002/0022883 A1 | 2/2002 | Burg |
| 2005/0070930 A1 | 3/2005 | Kammerer |

OTHER PUBLICATIONS

"Characterization of permeability and network structure of interfacially photopoymerized poly(ethylene glycol) diacrylate hydrogels," by G. M. Cruise, D.S. Scharp, and J.A. Hubbel; *Biomaterials 19* (1998), Elseveir Science Ltd., pp. 1287-1294.

"Bridging Areas of Injury in the Spinal Cord," by Mary Bartlett Bunge, The Neuroscientist, vol. 7, No. 4, 2001, Sage Publications, pp. 325-339.

\* cited by examiner

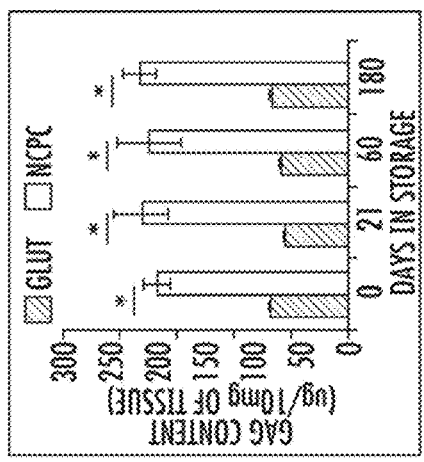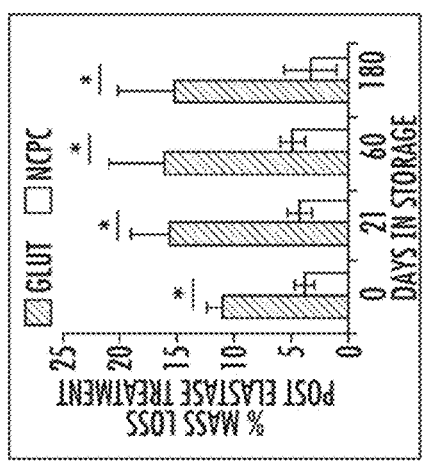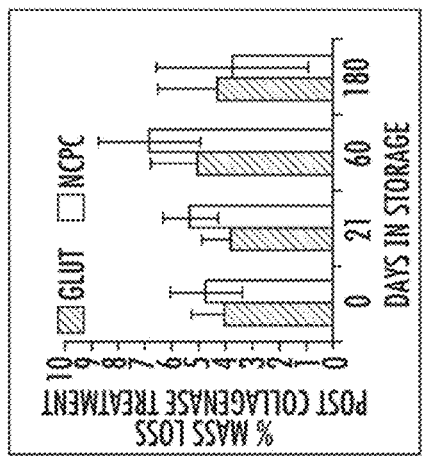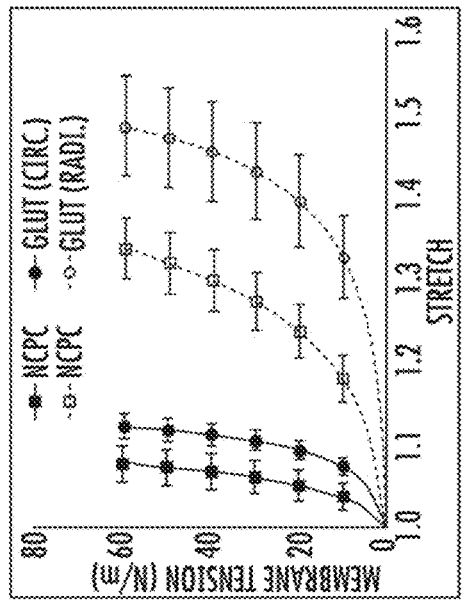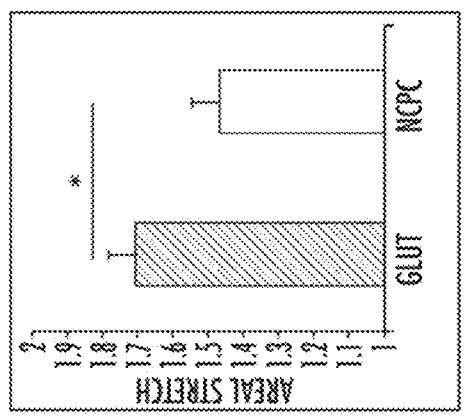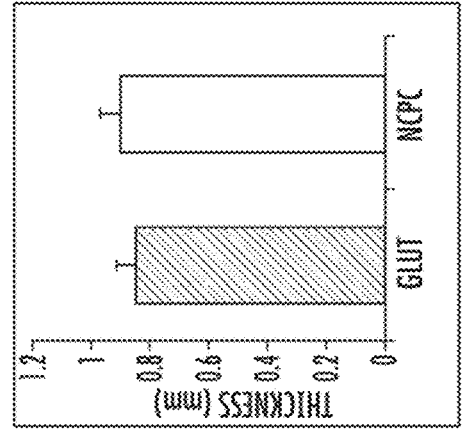

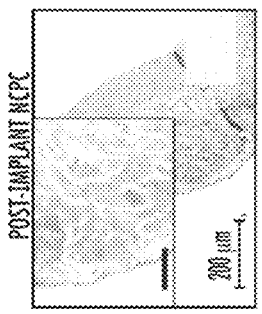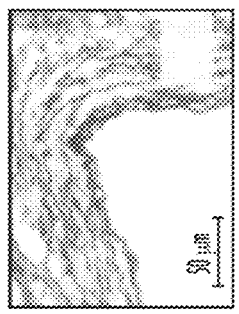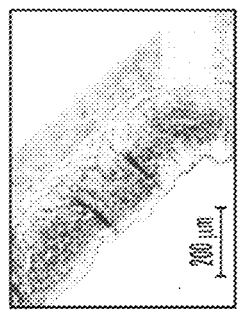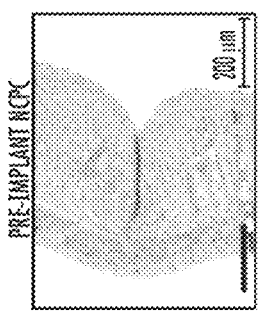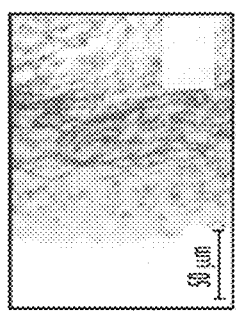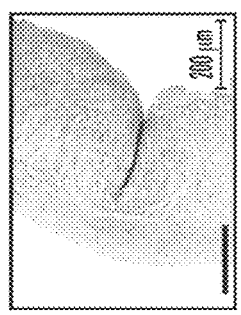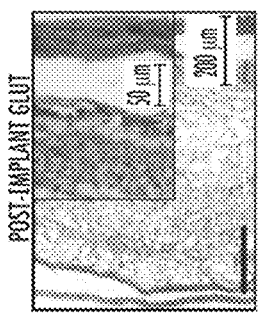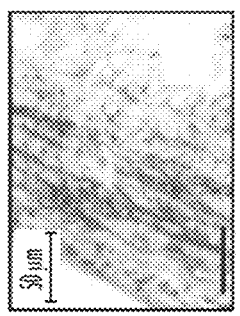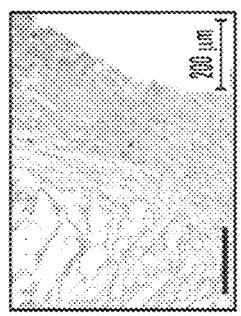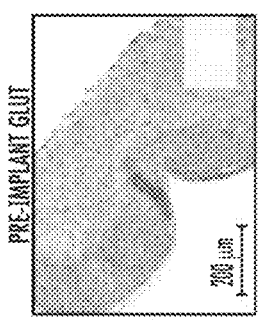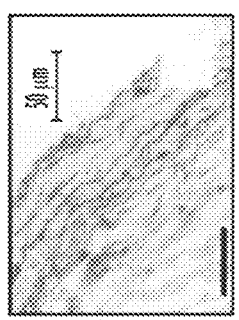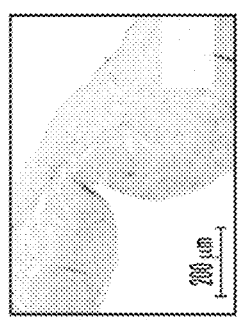

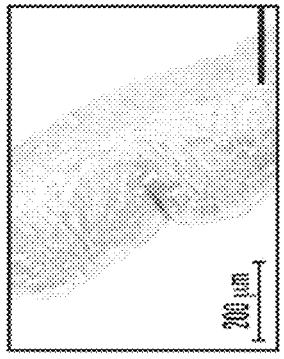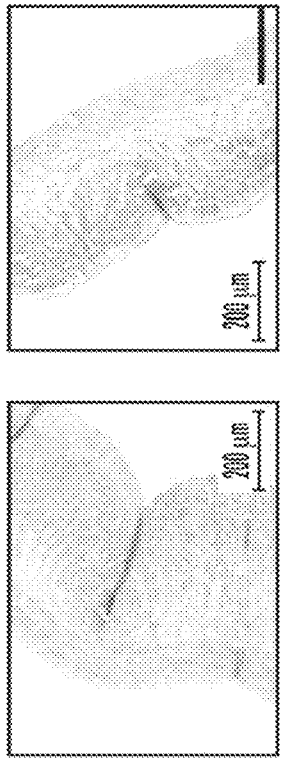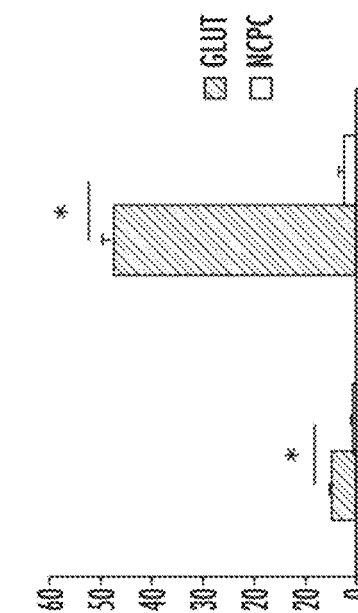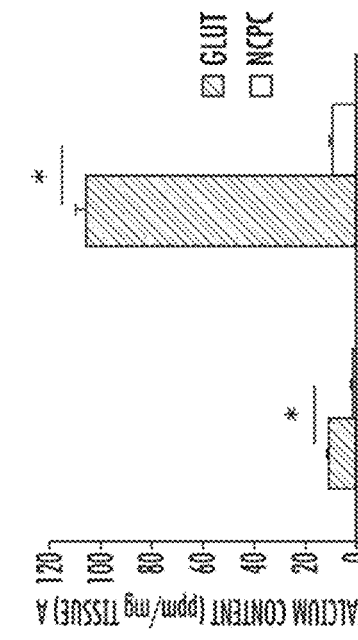

MULTI-STEP CONNECTIVE TISSUE STABILIZATION METHOD AND STABILIZED TISSUE FORMED THEREBY

CROSS REFERENCE TO RELATED APPLICATION

This application claims filing benefit of U.S. Provisional Patent Application Ser. No. 61/881,611 having a filing date of Sep. 24, 2013, which is incorporated herein by reference in its entirety.

STATEMENT AS TO RIGHTS TO INVENTIONS MADE UNDER FEDERALLY SPONSORED RESEARCH

This invention was made with Government support under Contract No. R01 HL108330 and R01 HL070969 awarded by the National Institutes of Health. The Government has certain rights in the invention.

BACKGROUND

Connective tissue is the framework upon which other tissue types, i.e., epithelial, muscle, and nervous tissues, are supported. Connective tissue generally includes individual cells not directly attached to one another and held within the extracellular matrix. The extracellular matrix, in turn, includes the ground substance, e.g., the minerals of bone, the plasma of blood, etc.; cell and tissue supporting materials including glycosaminoglycans (GAGs); and structural proteinaceous components including collagen fibers and elastin fibers. Glycosaminoglycans (GAGs) are long unbranched polysaccharides present in the connective tissue layer of many materials suitable for forming implants. GAGs promote cell proliferation, wound repair and tissue hydration and can act as a shock absorber or cushioning agent in a tissue.

Connective tissue can assume widely divergent architectures, ranging from blood, in which the fibrous component is absent and the ground substance is fluid, to dense connective tissue, which includes a relatively high proportion of extracellular fibers (e.g., collagen) and may contain low concentrations of other connective tissue components. There are many specialized types of connective tissue, one example being elastic tissue, in which elastic fibers are the major component of the tissue and the amount of factors commonly found in other types of connective tissue, such as collagen and proteoglycans, may be minimal.

The degeneration of the structural proteins in connective tissue is associated with many pathologic conditions include aneurysm, Marfan syndrome, supravalvular aortic stenosis, and chronic obstructive pulmonary disease (COPD). For those afflicted, such conditions lead to, at the very least, a lowered quality of life. Current methods of treatment for degeneration of connective tissue are limited. For instance, aneurysm treatment methods are often limited to invasive surgical techniques including stent repair or vascular graft. Unfortunately, surgical solutions include high risk of complication due to, e.g., neurological injuries, bleeding, or stroke as well as implant-related complications such as thrombosis, leakage or implant failure.

Accordingly, methods and materials that can provide stabilization of connective tissue would be highly beneficial.

Connective tissue is also commonly present in implantable bioprosthetics. For instance, bioprosthetic heart valves, which consist primarily of bovine pericardium and porcine aortic heart valve, are utilized in forming bioprosthetic heart valves for replacement of damaged natural valves. Bioprosthetic heart valves include allograft valves, which include biomaterial supplied from human cadavers; autologous valves, which include biomaterial supplied from the individual receiving the valve; and xenograft valves, which include biomaterial obtained from non-human biological sources including pigs, cows or other animals. Bioprosthetic heart valves can be used to replace damaged or diseased heart valves including aortic, mitral, and pulmonary valves.

Allograft transplants have been quite effective, with good compatibility and blood flow characteristics in the recipients. However, the availability of human valves for transplantation continues to decline as a percentage of cardiac surgeries performed each year. As such, the choice of xenograft materials for use in replacement BPHVs is becoming more common.

Both xenografts and allografts require that the graft biomaterial be stabilized via chemical fixation prior to use in order to render the biomaterial more non-antigenic as well as to improve resistance of the biomaterial to degradation. Currently, glutaraldehyde fixation of implantable biomaterial is used. Glutaraldehyde fixation forms covalent cross-links between free amines in the collagen of the connective tissue. Glutaraldehyde is commonly used alone as well as in combination with a variety of other compounds in stabilizing tissues for implant. For instance, traditional glutaraldehyde fixation methods are adequate for fixing collagen, but this method is not adequate for fixing other extra cellular matrix components of a tissue. For example, GAGs are not fixed via glutaraldehyde crosslinking regimes. As GAGs of the spongiosa layer can act as a cushion between the outer fibrosa and ventricularis layers during function, the leaching of GAGs from implantable materials can lead to reduced bending stiffness and ultimately to degenerative failure of the implant. Attempts have been made to stabilize GAGs in implantable tissues. While these methods have shown some success in preventing degradation of implant materials, room for improvement exists.

Stabilization regimes used alone or in conjunction with glutaraldehyde fixation protocols include use of polyepoxy amines for crosslinking a variety of amino acid residues found in tissue proteins (see, e.g., U.S. Pat. No. 6,391,538 to Vyavahare, et al., which is incorporated herein by reference), use of phenolic tannins for elastin fixation (see, e.g., U.S. Pat. No. 7,713,543 to Vyavahare, et al., which Is Incorporated herein by reference), and use of various chemistries including carbodiimide chemistry for stabilization of glycosaminoglycans in biological tissues (see, e.g., U.S. Pat. No. 6,861,211 to Levy, et al., U.S. Pat. No. 7,918,899 to Girardot, et al., and U.S. Pat. No. 7,479,164 to Girardot, et al., which are incorporated herein by reference).

Despite advances in addressing the needs for longer lasting and better performing implantable bioprosthetics, there remains room for variation and improvement within the art.

SUMMARY

Disclosed in one embodiment is a method for stabilizing connective tissue. For example, the method can include three consecutive fixation steps for connective tissue that includes collagen, elastin, and glycosaminoglycans. The first step includes contacting the connective tissue with a glycosaminoglycanase (GAGase) inhibitor. The GAGase inhibitor can include amine groups and the GAGase inhibitor can bind to components of the connective tissue through formation of amide bonds with free carboxyl groups of the tissue components.

The second step of the method can include contacting the connective tissue with a solution that includes a first crosslink activator and/or a phenolic compound. The first crosslink activator can encourage bond formation between and among collagen proteins of the tissue, as well as between collagen proteins and the GAGase inhibitor, and the phenolic compound can stabilize elastin of the connective tissue.

The third step of the stabilization process can include contacting the connective tissue with a second crosslink activator. The second crosslink activator can be the same or different as the first crosslink activator and can encourage bond formation between and among collagen proteins of the tissue, as well as between collagen proteins and the GAGase inhibitor, similar to the first crosslink inhibitor.

Also disclosed are connective tissues that have been stabilized according to the method. The connective tissue can be very stable following contact with collagenase and elastase. For instance, the stabilized connective tissue can exhibit about 5% or less weight loss following contact with collagenase for 48 hours and can exhibit about 10% or less weight loss following contact with elastase for 24 hours. The stabilized connective tissue can also exhibit GAG retention over time. For instance, the stabilized connective tissue can exhibit a GAG concentration of greater than about 150 micrograms (μg) per 10 milligrams (mg) of tissue following treatment with GAGase.

BRIEF DESCRIPTION OF THE FIGURES

A full and enabling description of the disclosed subject matter, including the best mode thereof, to one of ordinary skill in the art, is set forth more particularly in the remainder of the specification, including reference to the accompanying figures in which:

FIG. 2 presents the long-term crosslinking stability of crosslinked porcine aortic valve leaflets. GLUT or NCPC treated leaflets were challenged with collagenase (FIG. 2A) or elastase (FIG. 2B) and percent mass lost was utilized to determine biochemical effectiveness of crosslinking at 0, 21, 60, or 180 days of storage (n=6). GLUT or NCPC treated leaflets were challenged with GAGase and hexosamine content was utilized to determine GAG stability at 0, 21, 60, or 180 days (n=8) (FIG. 2C). *Indicates significant difference (p<0.05) from GLUT.

FIG. 3 presents the results of equibiaxial mechanical testing on GLUT and NCPC specimens (n=7 for both). FIG. 3A illustrates no significant difference in the thickness of the GLUT and NCPC treated specimens. The area stretch at 60 N/m shows a difference in the compliance between GLUT and NCPC treated specimens (FIG. 3B). The mean equibiaxial mechanical response is shown in FIG. 3C and includes the standard error of the mean.

FIG. 4 illustrates the histological characterization of host cellular response and ECM integrity of GLUT and NCPC treated porcine aortic valve leaflets pre or post in vivo implantation into male juvenile rats for 90 days. FIG. 4A, FIG. 4B, FIG. 4C, and FIG. 4D are hemotoxylin and eosin staining for pre- and post-implant for GLUT treatment and NCPC treatment, respectively. Nuclei are stained darker than cytoplasm. Calcification nodules are granular and stained very dark. Black bar indicates 200 μm and 50 μm in insets, respectively. FIG. 4E, FIG. 4F, FIG. 4G, and FIG. 4H present Movat's Pentachrome staining for pre- and post-implant for GLUT treatment and NCPC treatment, respectively. Fibrous elastin is stained dark. Black bar indicates 50 μm. FIG. 4I, FIG. 4J, FIG. 4K, and FIG. 4L present Alcian blue staining for pre- and post-implant for GLUT treatment and NCPC treatment, respectively. GAGs and nuclei are stained. Black bar indicates 200 μm.

FIG. 5 presents the mineralization characterization in crosslinked porcine aortic valve leaflets pre- or post-in vivo implantation into male juvenile rats for 90 days. FIG. 5A, FIG. 5B, FIG. 5C, and FIG. 5D are Alizarin red staining for calcification deposits counterstained after 90 days implantation. Black bar indicates 200 μm. FIG. 5A is pre-implantation GLUT, FIG. 5B is pre-implantation NCPC, FIG. 5C is post-implantation GLUT, and FIG. 5D is post-implantation NCPC. FIG. 5E and FIG. 5F presents the ICP determination (n=6) of calcium (FIG. 5E) and phosphorus (FIG. 5F) mineral content at 0, 30, or 90 days. *Day 0 implants had no detectable amount of mineralization. *Indicates significant difference (p<0.05).

DETAILED DESCRIPTION

Figure 1B:
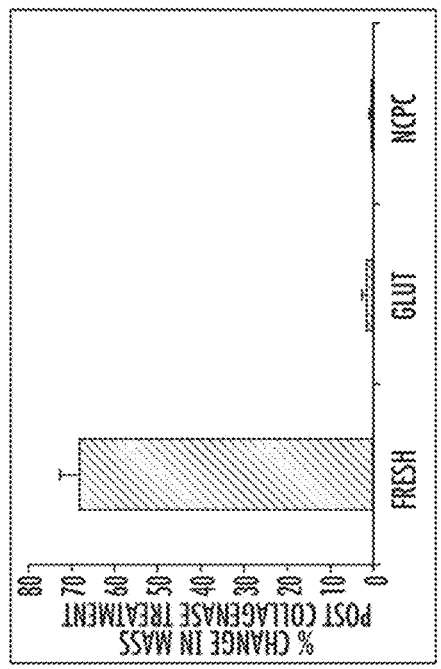
FIG. 1 illustrates extracellular matrix (ECM) stability of crosslinked porcine aortic valve leaflets including FIG. 1A, which illustrates differential scanning calorimetry (DSC) analysis of the denaturing temperature of leaflets treated according to traditional glutaraldehyde fixation methods (GLUT) and methods as disclosed herein (NCPC). Also shown is the percentage change in mass of fresh and fixed leaflets following treatment with collagenase (FIG. 1B) and elastase (FIG. 1C) (percent mass lost was utilized to determine biochemical effectiveness of crosslinking (n=6)).
FIG. 1D presents the GAG content of fixed leaflets following challenge with either GAGase or buffer solution. Hexosamine content was utilized to determine GAG stability. *Indicates significant difference (p<0.05) from GLUT.

Reference now will be made in detail to embodiments of the disclosed subject matter, one or more examples of which are set forth below. Each example is provided by way of explanation, not limitation of the subject matter. In fact, it will be apparent to those skilled in the art that various modifications and variations can be made without departing from the scope or spirit of the disclosure. For instance, features illustrated or described as part of one embodiment can be used on another embodiment to yield a still further embodiment. Thus, it is intended that the present disclosure cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects, which broader aspects are embodied in the exemplary constructions.

Definitions

As used herein the term "bioprosthesis" includes any prosthesis which is derived in whole or in part from human, animal, or other organic tissue and which can be implanted into a human or an animal. For example, the term "bioprosthesis" can include, without limitation, an artificial heart, a heart valve prosthesis, an annuloplasty ring, a dermal graft, a vascular graft, a vascular, cardiovascular, or structural stent, a vascular or cardiovascular shunt, a dura mater graft, a cartilage graft, a cartilage implant, a pericardium graft, a ligament prosthesis, a tendon prosthesis, a urinary bladder prosthesis, a pledget, a suture, a permanently or temporary in-dwelling percutaneous device, an artificial joint, an artificial limb, a bionic construct (i.e. a bioprosthesis comprising a microprocessor or other electronic component), and a surgical patch.

As used herein, the term "tissue" is intended to include any natural or synthetic material derived from an organic source and which may be implanted in a mammal. For instance, in addition to natural tissues, the term can include synthetic analogs of natural tissues such as tissue engineered constructs that can include natural biological components, synthetic components, or combinations of such. While exemplary forms of a tissue are described herein, the term "tissue" is not limited to the exemplary embodiments but may include other types of tissues having properties similar to the exemplary tissue.

As used herein, the term "crosslink" refers generally to the process of forming bonds, e.g., covalent bonds, between free, active moieties on or within tissue or between a crosslinking agent or other compound which reacts with a reactive moiety of a tissue. The resulting crosslinked tissue can be considered fixed.

As used herein, the term "fixed," and "stabilized," and grammatical forms thereof are used interchangeably and refer to tissue that has been treated so as to be less antigenic and less susceptible to physical and/or biological degradation. The terms can refer to methods for increasing the mechanical strength of a tissue or a bioprosthesis incorporating a tissue, decreasing the rate or incidence of degradation of a tissue or a bioprosthesis incorporating a tissue following its in vivo application or implantation, or a combination of methods. Stabilization can enhance one or more of the durability, shelf life, and fatigue life of a bioprosthesis.

Description

In general, the present disclosure is directed to methods for improving the structural and mechanical characteristics of implantable tissue as well as methods for increasing the lifespan of implantable tissues. The disclosure is also directed to implantable tissues formed according to the disclosed methods. More specifically, the disclosed methods can include a multi-step process that provides a route to chemically and physically stabilizing all of the collagen, elastin, and GAG components of connective tissue. Through the disclosed methods, implantable tissues can exhibit increased resistance to degradation including degradation due to enzyme activity following implantation of the tissues, fatigue, and storage. Disclosed methods can lead to increased levels of beneficial ECM components remaining in the stabilized implantable tissues as compared to previously known stabilized implantable tissues. Increased levels of such components can further improve the implantable tissues through improved mechanical characteristics and can also lead to longer lifespan of a bioprosthesis. Moreover, the disclosed methods can stabilize the components of connective tissue without the use of previously known fixatives. For instance, the stabilized connective tissue can be glutaraldehyde-free while exhibiting improved collagen stabilization as compared to tissues stabilized according to previously known glutaraldehyde fixation methods.

By way of example, connective tissue stabilized according to the disclosed methods can exhibit much lower weight loss following contact with elastase and collagenase as compared to non-stabilized tissue and tissue stabilized according to traditional glutaraldehyde stabilization methods. For instance, the stabilized tissue can exhibit about 5% or less, about 3% or less, or about 1% or less weight loss following treatment with collagenase for 48 hours. Similarly, the stabilized tissue can exhibit about 10% or less, about 5% or less, or about 3% or less weight loss following treatment with elastase for 24 hours.

The GAG component of the connective tissue can also be stabilized by use of the disclosed methods and the tissue can exhibit improved GAG retention over time. For instance, the stabilized tissue can exhibit a GAG concentration of greater than about 150 µg/10 mg of tissue, greater than about 200 µg/10 mg of tissue, or greater than about 250 µg/10 mg of tissue following treatment with a GAGase.

Following implantation, the stabilized tissue can resist mineralization. For instance, the calcium content following implantation can be less than about 80 parts per million (ppm)/10 mg tissue, less than about 50 ppm/10 mg tissue, less than about 30 ppm/10 mg tissue, or less than about 20 ppm/10 mg tissue. For instance, the calcium content following implantation can be about 10 times less than that of tissues fixed according to traditional glutaraldehyde processing methods under similar implantation methods and for similar implantation periods. For example, 30 days following implantation, the stabilized tissue can exhibit a calcium content of about 10 ppm calcium/mg dry tissue or less, about 5 ppm calcium/mg dry tissue or less, or about 2 ppm calcium/mg dry tissue or less. 90 days following implantation, the stabilized tissue can exhibit a calcium content of about 20 ppm calcium/mg dry tissue or less, about 15 ppm calcium/mg dry tissue or less, or about 10 ppm calcium/mg dry tissue or less. In comparison, a tissue fixed according to traditional glutaraldehyde fixation techniques can have a calcium content after 30 days implantation of about 10-15 ppm/mg dry tissue and after 90 days implantation of about 100-110 ppm/mg of dry tissue.

The phosphorous content of the disclosed fixed tissues following implantation can be less than about 50 ppm/10 mg tissue, less than about 30 ppm/10 mg tissue, less than about 20 ppm/10 mg tissue, or less than about 10 ppm/10 mg tissue. The phosphorous content can be about 10 times less than that of tissue fixed according to traditional glutaraldehyde processing methods under similar implantation methods and for similar implantation periods. For instance, 30 days following implantation, the phosphorous content of the fixed tissue can be about 3 ppm/mg dry tissue, about 1 ppm/mg dry tissue, or about 0.6 ppm/mg dry tissue in some embodiments. 90 days following implantation, the phosphorous content of the fixed tissue can be about 5 ppm phosphorous/mg dry tissue, about 3 ppm/mg dry tissue, or about 2.5 ppm/mg dry tissue in some embodiments. In comparison, a tissue fixed according to traditional glutaraldehyde fixation techniques can have a phosphorous content after 30 days implantation of about 1-10 ppm/mg dry tissue and after 90 days implantation of about 45-50 ppm/mg dry tissue.

The stabilized tissue can exhibit excellent biomechanical response. For instance, the stabilized tissue can exhibit a peak radial stress of about 60 kiloPascals (kPa) or greater, for instance about 90 kPa or greater or about 100 kPa or greater and can exhibit a peak circumferential stress of about 60 kPa or greater, about 90 kPa or greater, or about 100 kPa or greater. The stabilized tissue can exhibit a strain of about 1.1 or greater, about 1.2 or greater, or about 1.3 or greater.

Implantable connective tissue as may be stabilized according to the method can be derived from xenograft, allograft, or autologous tissue. Biological tissue can be of either human or animal origin. Thus, a bioprosthetic can be a xenograft prosthetic, an allograft prosthetic, an autologous prosthetic, or a can include a combination of tissues from a combination of different sources. Disclosed methods can also be utilized in stabilizing synthetic tissues such as tissue engineered constructs.

In general, the connective tissue can include elastin, collagen, and one or more GAGs and can be obtained according to tissue culture techniques as are generally known in the art, and thus, such techniques are not discussed in detail herein. When considering natural connective tissue, any suitable biological source that includes connective tissue can be utilized including, without limitation, cardiac structures (e.g., heart valve, aortic root, aortic wall, aortic leaflet, pericardium, etc.), dura mater, tendon, ligament, dermal structures, blood vessels, umbilical materials, vein, pericardium, fascia, submucosa, and the like. Thus, the implantable material can include multiple tissue types, with the connective tissue being one component of the implantable material.

The multi-step stabilization method includes a first step in which the connective tissue is incubated with a GAGase inhibitor. For instance, an implantable structure including the connective tissue (e.g., a heart valve leaflet that includes at least one layer of connective tissue) can be incubated in a solution of the GAGase inhibitor. The concentration of the GAGase inhibitor in the treatment solution is not particularly limited, and can vary depending upon the volume of connective tissue to be stabilized. For example, a solution can include the GAGase inhibitor in a concentration of about 0.2 millimolar (mM) or greater, or about 0.3 mM or greater, and the structure including the connective tissue can be incubated in a solution of the GAGase inhibitor for a period of about 30 minutes or more, for instance about 1 hour or more, such that the GAGase inhibitor can contact the connective tissue of the implantable structure.

Specific GAGase inhibitors that can be utilized can depend upon the other components in the fixed tissue, both endogenous and exogenous components, as well as the specific application of the tissue, e.g., the implant environment. In general, the GAGase inhibitor will be a non-endogenous component of the tissue.

One or more GAGs as may be either naturally or synthetically incorporated in an implantable tissue can be stabilized through the binding in the tissue of the GAGase inhibitor that can inhibit enzyme(s) that hydrolyze or otherwise cleave the GAGs. Moreover, GAGs that can be stabilized in and on the bioprosthesis can be either endogenous or exogenous. Typical GAGs as may be stabilized can include, for example, hyaluronic acid (also known as hyaluronan and hyaluronate), chondroitin sulphate, keratan sulphate, dermatan sulphate, heparan sulphate, and the like.

In general, any GAGase inhibitor or combination thereof can be utilized to stabilize connective tissue according to the presently disclosed methods. For example, sulfated oligosaccharides including sulfated verbascose, planteose and neomycin can be incorporated into a tissue. Apigenin, a flavone and known hyaluronidase inhibitor can also be utilized. Ascorbyl palmitate, tetradecyl sodium sulphate, indomethacin, hesperidin phosphate, sodium aurothiomalate and glycyrrhizin are other known hyaluronidase inhibitors that can be utilized.

In one embodiment, the connective tissue can be stabilized through treatment of the tissue with the GAGase inhibitor neomycin. Neomycin's chemical structure is:

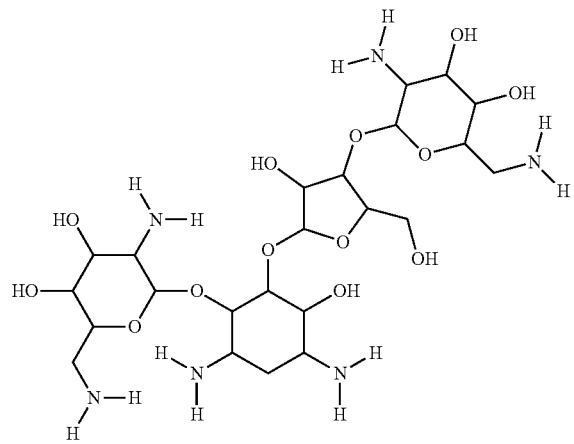 [SMILES: NCC1OC(OC2C(CO)OC(OC3C(O)C(N)CC(N)C3OC3OC(CN)C(O)C(O)C3N)C2O)C(N)C(O)C1O]

Neomycin has been found to be effective as a GAGase inhibitor, particularly when in the salt form of the compound. For example, an implantable material that includes connective tissue can be incubated with a sulfate salt of neomycin. For instance, an implantable material can be incubated with solution of the neomycin (e.g. a neomycin sulfate salt solution) for a period of time such that the neomycin can contact the connective tissue of the implantable material.

In one embodiment, the GAGase inhibitor can be covalently bound in the connective tissue via reaction of an amine group of the GAGase inhibitor with a carboxyl group of another tissue component, for instance an endogenous tissue component such as collagen or a GAG, to form an amide bond. As can be seen, neomycin includes multiple free amines and as such, multiple amide bonds can be formed between a single neomycin molecule and other components of a tissue. Accordingly, the addition of neomycin (and/or another multi-amine containing GAGase inhibitor) to a tissue during a stabilization process can not only provide enzyme inhibition activity to the tissue following implant, but can also provide crosslinking activity during the treatment protocol and can stabilize carboxyl-containing tissue components in the connective tissue.

It should be understood that the stabilization method is not limited to utilization of neomycin GAGase inhibitors. For example, in one embodiment, heparin, which is a hyaluronidase inhibitor (see, e.g., Am J Cardiol. 1984 Mar. 15; 53(7):941-4) can be utilized to stabilize the connective tissue.

Following treatment of the connective tissue with the GAGase inhibitor, a second treatment step can be carried out during which the connective tissue can be incubated with a solution including a crosslink activator and/or a phenolic compound. This incubation can be carried out over a period of several hours, for instance about 12 hours or more, or about 24 hour or more, in one embodiment.

The crosslink activator can encourage crosslinking between and among components of the connective tissue. For example, the crosslink activator can encourage binding between amine-containing and carboxyl-containing components in the connective tissues. In one embodiment, the crosslink activator can encourage bond formation between carboxyl and amine groups of collagen and/or other proteinaceous components of the connective tissue. The crosslink activator can likewise encourage bond formation between amine groups of the GAGase inhibitor and carboxyl groups of the collagen proteins.

In one embodiment, the crosslink activator can utilize carbodiimide chemistry to activate a carboxyl group of a connective tissue component. Exemplary crosslink activators include carbodiimides such as 1-ethyl-3-(3 dimethylaminopropyl) carbodiimide (EDC).

The solution can include the crosslink activator in a concentration that can vary depending upon the volume of tissue to be treated. For instance, the solution can include the crosslink activator in a concentration of about 10 mM or greater, about 20 mM or greater, or about 30 mM or greater.

In one embodiment, the solution utilized in the second step of the stabilization process can include a crosslinking agent. For instance, epoxy reagents, heterobifunctional reagents, heterofunctional azides, carbohydrate-protein linking reagents and the like, can be utilized that can react with tissue components and form crosslinks within the stabilized tissue. As utilized herein, a crosslinking agent is a compound that reacts with the tissue components, and the crosslinked reaction product includes the reaction product of the crosslinking agent. In contrast, a crosslink activator does not become a part of the formed crosslink, but rather functions to encourage the formation of a crosslink bond between two other components. Common heterobifunctional crosslinking agents suitable for use include, without limitation, those having one or more amine-reactive groups, e.g., a succinimidyl ester (i.e., NHS-ester) at one terminus and a sulfhydryl reactive group at another terminus. The sulfhydryl-reactive groups can be, for example, maleimides, pyridyl disulfides or α-haloacetyls. Suitable heterobifunctional reagents can also have one reactive group that is photoreactive rather than thermoreactive.

In addition to or alternative to the crosslink activator and optional crosslinking agent, the solution of the second step can include a phenolic compound that can stabilize the elastin component of the connective tissue. Phenolic compounds encompassed herein generally include compounds that include at least one phenolic group bound to a hydrophobic core. While not wishing to be bound by any particular theory, it is believed that interaction between the phenolic compound and the elastin involves both the hydroxyl group(s) and the hydrophobic core of the phenolic compound. It is believed that the phenolic compounds can stabilize elastin proteins through both steric means and bond formation and thereby protect sites on the protein susceptible to enzyme-mediated (e.g., elastase or MMP-mediated) cleavage.

Specifically, it is believed that hydroxyl groups of a phenolic compound can bind elastin multivalently, for instance via hydrogen bond formation with amino acid residues such as polar amino acid residues including methionine, glycine and proline, such that multiple proteins can interact with a single phenolic compound to create a three-dimensional cross-link structure involving multiple elastin molecules. Moreover, the phenolic compound can optionally include one or more double bonds, with which the phenolic compounds can covalently bind to the elastin, forming an even stronger and more permanent protective association between the phenolic compound and the elastin of the connective tissue. In addition, the large hydrophobic regions of the elastin protein, which are believed to contain sites susceptible to elastase-mediated cleavage, are also believed to contain sites of association between the hydrophobic core of the phenolic compound and the protein. Thus, the association between the phenolic compound and the protein molecules is believed to protect specific binding sites on the protein targeted by enzymes through the association of the protein with the hydrophobic core and can also sterically hinder the degradation of the protein through the development of the large three dimensional cross-link structure.

Phenolic compounds can include, but are not limited to, flavonoids and their derivatives (e.g., anthocyanins, quercetin), flavolignans, phenolic rhizomes, flavan-3-ols including (+)-catechin and (−)-epicatechin, other tannins and derivatives thereof (such as tannic acid, pentagalloylglucose, nobotanin, epigallocatechin gallate, and gallotannins), ellagic acid, procyanidins, and the like.

Phenolic compounds can include synthetic and natural phenolic compounds. For example, natural phenolic compounds can include those found in extracts from natural plant-based sources such as extracts of olive oil (e.g., hydroxytyrosol (3,4-dihydroxyphenylethanol) and oleuropein, extracts of cocoa bean that can contain epicatechin and analogous compounds, extracts of *Camellia* including *C. senensis* (green tea) and *C. assaimic*, extracts of licorice, sea whip, aloe vera, chamomile, and the like.

In one embodiment, the phenolic compound can be a tannin or a derivative thereof. Tannins can be found in many plant species. For example, the tea plant (*Camellia sinensis*) has a naturally high tannin content. Green tea leaves are a major plant source of tannins, as they not only contain the tannic and gallic acid groups, but also prodelphinidin, a proanthocyanidin. Tannins are also found in wine, particularly red wine as well as in grape skins and seeds. Pomegranates also contain a diverse array of tannins, particularly hydrolysable tannins.

Tannic acid, the structure of which is provided below, is a common naturally derived tannin.

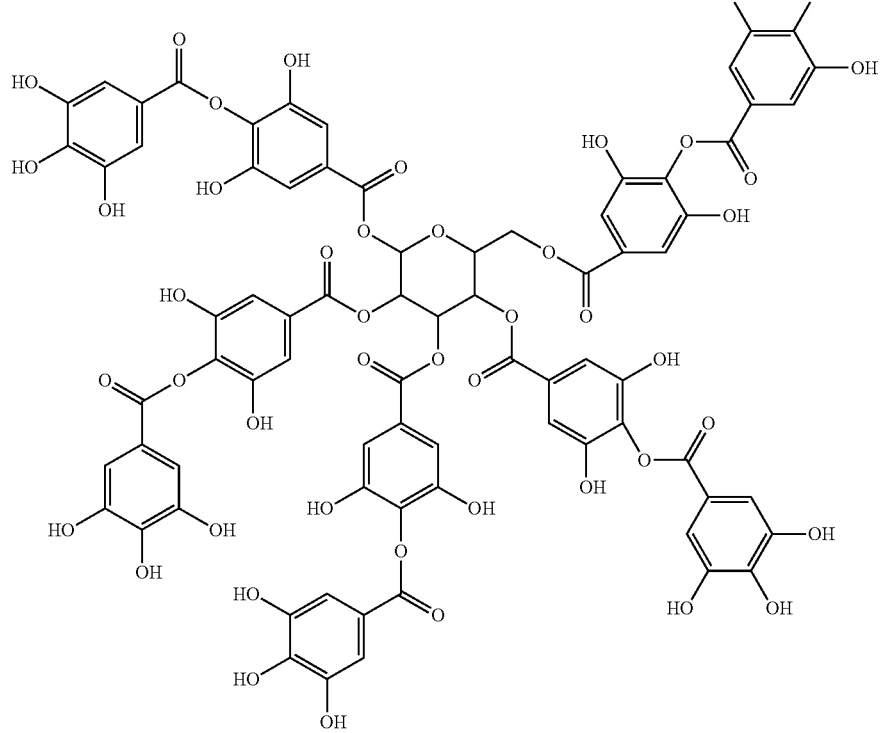

Tannic acid can interact with other connective tissue components as well as elastin, and thus can stabilize additional components of the targeted connective tissue in the stabilization process, in addition to the elastin component. For instance, tannic acid is capable of cross-linking GAGs as well as other connective tissue components.

In one embodiment, the stabilization of connective tissue can be carried out in vivo. Accordingly, in such embodiments, biocompatibility and cytotoxicity of the agents can be of importance in preparation of therapeutics including the disclosed compounds. At one time, tannic acid-containing preparations were suspected of causing hepatoxicity. This toxicity has since been primarily attributed to poor purity of the preparations and the inclusion of toxic gallic acid residues in the compositions. Accordingly, in one embodiment, the stabilization method can utilize high purity tannic acid, with little or no free gallic acid residue included in the compositions. For example, in one embodiment, the compositions of the present invention can include less than about 5% free gallic acid residue in the preparation. In one embodiment, the compositions of the present invention can include between about 1% and about 5% free gallic acid residue in the composition.

In embodiment, the second step of the stabilization method can utilize an effective amount of pentagalloylglucose (PGG), the structure of which is provided below:

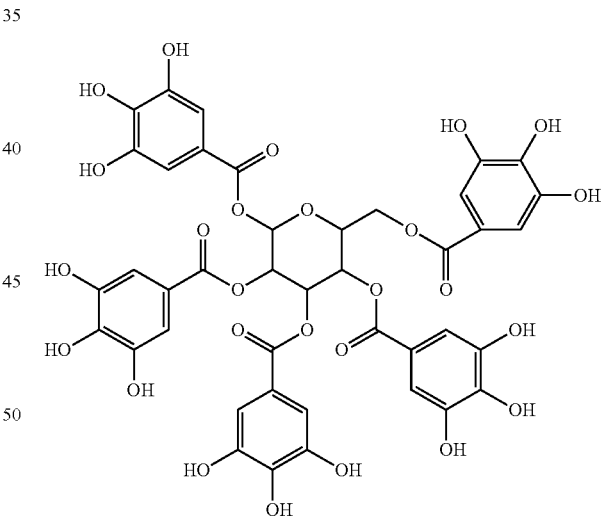

PGG, which is the central portion of a tannic acid molecule, includes the hydrophobic core of tannic acid as well as multiple phenolic hydroxy groups, but does not possess the outer gallic acid residues and the hydrolyzable ester bonds associated with tannic acid. Thus, the possibility of release of free gallic acid residues over the course of a long-term application process can be prevented through utilization of a compound having no gallic acid residues, such as PGG, as the selected phenolic agent.

The composition of the second step can include one or more phenolic compounds in a concentration that can vary over a wide range, with a preferred concentration generally depending on the particular application and the volume of tissue to be stabilized. For example, a solution including a crosslink activator and a phenolic compound can include the phenolic compound in a concentration of about 3 mM or greater, about 4 mM or greater, or about 5 mM or greater. It should be noted, however, that while these exemplary concentrations are effective in certain embodiments, a wider range of phenolic compound concentrations may be utilized. For example, actual concentrations used may be influenced by the tissue targeted by the procedure, size of the targeted area, desired incubation time, and preferred pH, in addition to delivery mode, as mentioned above.

As a third step in the stabilization process, the connective tissue can be incubated with a crosslink activator a second time. The crosslink activator utilized in the third step can be the same or different as the crosslink activator of the second step, and the crosslink activator can be provided in a concentration similar to that of the second step. For instance, the connective tissue can be incubated in a solution of the crosslink activator at a concentration of about 10 mM or greater, about 20 mM or greater, or about 30 mM or greater, in one embodiment. The incubation time for the third step can generally be at least several hours, for instance about 12 hours or more, or about 24 hours or more, in one embodiment.

The solution utilized in the third stabilization process can optionally include a crosslinking agent in conjunction with the crosslink activator. For instance, heterofunctional crosslinking agents such as those including one or more amine-amine reactive and/or amine-sulfhydryl reactive groups can be utilized, as discussed previously.

The stabilization method can also include the stabilization of non-proteinaceous components of an implantable tissue as well as binding of additional beneficial components in or on a stabilized tissue. Component can be either exogenous or endogenous components. Other components that can be included in an implantable tissue via covalent binding, ionic binding, hydrogen bonding, or any other incorporation method can include, without limitation, polyepoxy amine compounds, buffering agents, physiological salts, calcification inhibitors, and the like. For instance, research has suggested that ethanol pretreatment and pre-incubation before implantation has reduced calcification greatly. Accordingly, in one embodiment, disclosed stabilization protocols can include an ethanol treatment regime, as is generally known in the art.

Bioprosthetic implants that incorporate the stabilized connective tissue, such as a bioprosthetic heart valve implant for example, can be subject to a great deal of motion following implantation. For instance, during the cardiac cycle valvular cusps are continuously subjected to tensile, compressive, and shear stresses. The interlayer shearing between the fibrosa and ventricularis is mediated by the medial spongiosa layer. GAGs of the connective tissue, hydrophilic in nature, form a gel-like layer in the spongiosa capable of distributing and dissipating these valvular stresses. Stabilization of the components of the connective tissue as described herein can maintain this layer throughout the life of the implant.

In one embodiment, the stabilization method can be utilized in an in vivo treatment protocol, and the three stabilization solutions can be targeted to connective tissue in a sequential fashion. For instance, a diagnosed aneurysm can be targeted for sequential delivery of the stabilization compounds using minimally invasive procedures to provide delivery of the treatment agents locally from a biocompatible implantable device.

Solutions of the stabilization compounds can be loaded in drug delivery vehicle(s) via encapsulation, coating, infusion, or any other loading mechanism as is known in the art so as to provide sequential delivery of the compounds according to the disclosed method. Prolonged absorption of an injectable form of the compounds may be brought about by the inclusion of agents, such as aluminum monostearate and gelatin, which can delay absorption of the compounds utilized in the second and third steps of the process. For example, injectable depot forms of the compounds utilized in the second and third steps can be made by forming microencapsule matrices including the compounds loaded in the matrix formed of biodegradable polymers such as polylactide-polyglycolide, poly(orthoesters) and poly(anhydrides). Depending upon the ratio of stabilizing compound to polymer and the nature of the particular polymer employed, the rate of drug release can be controlled. Depot injectable formulations can also be prepared by entrapping the stabilizing compound in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

In another embodiment, the stabilizing compounds can be sequentially targeted to connective tissue by use of hydrogel delivery vehicles. Hydrogels are herein defined to include polymeric matrices that can be highly hydrated while maintaining structural stability. Suitable hydrogel matrices can include un-crosslinked and crosslinked hydrogels. In addition, crosslinked hydrogel delivery vehicles of the invention can optionally include hydrolyzable portions, such that the matrix can be degradable when utilized in an aqueous environment, e.g., in vivo. For example, the delivery vehicle can include a cross-linked hydrogel including a hydrolyzable cross-linking agent, such as polylactic acid, and can be degradable in vivo.

Hydrogel delivery vehicles can include natural polymers such as glycosaminoglycans, polysaccharides, proteins, and the like, as well as synthetic polymers, as are generally known in the art. A non-limiting list of hydrophilic polymeric materials that can be utilized in forming hydrogels of the present invention can include dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

The delivery vehicles can include a combination of one or more delivery vehicles so as to deliver the stabilization compounds in the sequential fashion, as described. For instance, a hydrogel delivery vehicle can be combined with a patch, a stent, a perforated balloon, a vascular graft, or any other suitable device, for delivery of the stabilization compounds to connective tissue according to the sequential method.

The stabilization methods can also be utilized in conjunction with ex vivo tissue and in vitro tissue in the formation of a bioprosthetic implant. A stabilized implantable tissue can generally be utilized in any implantable bioprosthesis. For instance, the disclosure encompasses any of a variety of cardiac bioprostheses that can replace or support damaged sections of the cardiovascular system. For example, bioprosthetic heart valves, veins, or arteries are encompassed as well as other bioprostheses previously mentioned.

A bioprosthesis can include stabilized implantable tissue as herein disclosed in conjunction with other implantable support materials as are generally known in the art. For instance, a bioprosthesis can include disclosed implantable tissue in suitable combination with support materials such as forms, stents, suture rings, conduits, flanges, and the like.

In one embodiment, a bioprosthetic heart valve (BPHV) can be formed including heart valve leaflets that include stabilized connective tissue secured to a stent. Suitable stent materials can generally include stent materials as may generally be found in other known heart valves, including both mechanical and bioprosthetic heart valves. For example, tissue leaflets can be attached to a flexible polymer stent formed of, for instance, polypropylene reinforced with a metal ring (such as, for example, a Haynes™ alloy no. 25 metal ring). Polymeric stents are also known, such as a polymer stent including a polyester film support secured to a surgically acceptable metal ring such as an Elgiloy™ metal stiffener.

Optionally, a support material may be formed of only polymeric materials, and not include any metals. Alternatively, the disclosed bioprosthesis can include a metal support, e.g., a wire stent, such as an Elgiloy™ wire stent, or a titanium stent, which can optionally be covered with a cover, such as, for example, a fabric cover such as a Dacron™ fabric. In one embodiments, a bioprosthesis, e.g., an implantable BPHV, can include a sewing or suture ring such as, for example, a polyester, Dacron™, or Teflon™ suture ring, as is generally known in the art. In yet another embodiment, an implantable tissue can form a stentless heart valve. The specific make-up of any support material in a bioprosthesis is not critical to the disclosed subject matter.

Bioprostheses as may incorporate the stabilized implantable tissues are not limited, and any bioprosthesis that can beneficially include the stabilized tissue is encompassed herein. For instance, minimally invasive bioprosthetics such as minimally invasive transcatheter bioprosthetics can beneficially incorporate the disclosed stabilized tissue.

Following formation of a bioprosthetic device, e.g., a BPHV, the device can be implanted by any surgical procedure as is generally known in the art. For example, a BPHV including a stabilized tissue can be implanted in the heart of a person or an animal according to known surgical procedures such as, for example, procedures described in U.S. Pat. No. 6,532,388 to Hill, et al., U.S. Pat. No. 6,506,197 to Rollero, et al., and U.S. Pat. Nos. 6,402,780, 6,042,607, and 5,716,370 all to Williamson, I V, et al., all of which are incorporated herein by reference. In general, such procedures include removal of a damaged cardiac valve, implantation of the new replacement valve in the cardiac valve annulus, and attachment of the BPHV to the adjacent tissue.

Reference now will be made to exemplary embodiments set forth below. Each example is provided by way of explanation of the disclosure, not as a limitation.

Example 1

Porcine aortic heart valves (PAVs) were harvested fresh and transported on 0.9% saline and ice to the laboratory. Whole PAVs were washed in 0.9% saline for 15 minutes. The leaflets were then cut from the aortic root and washed in 0.9% saline for 3 to 5 minutes. These leaflets were then treated with two different chemical treatment techniques: (1) GLUT—current standard glutaraldehyde-based method and (2) NCPC-stabilization method as disclosed herein.

GLUT: Tissue was placed in 0.6% glutaraldehyde in 50 mM 4-(2-hydroxyethyl)-1-piperazineethanesulfonic acid (HEPES) buffered saline (pH 7.4) for 24 hours, solution decanted, and replaced with 0.02% glutaraldehyde in 50 mM HEPES buffered saline (pH 7.4) for at least six days.

NCPC:

Step 1: Tissues were placed into a 0.5 mM neomycin trisulfate salt solution in 2-(N-morpholino)ethanesulfonic acid (MES) buffer and incubated for 1 hour.

Step 2: The solution from Step 1 was decanted and the leaflets were then incubated in a 30 mM 1-ethyl-3-(3-dimethylaminopropyl) carbodiimide (EDC) and 6 mM N-hydroxysuccinimide (NHS)/0.05% PGG solution in 50 mM MES buffered saline (pH 5.5) for twenty-four hours.

Step 3: The solution from Step 2 was decanted and the leaflets were then incubated in a 30 mM EDC and 6 mM NHS solution in 50 mM MES buffered saline (pH 5.5) for 24 hours.

Following fixation, valves were placed in 20% isopropanol in 50 mM HEPES buffer (pH 7.4) for at least six days.

Collagen and elastin stability were assayed by treating either GLUT or NCPC leaflets with type VII collagenase for 48 hours or porcine pancreatic elastase for 24 hours and measuring the mass of the dry sample before and after enzyme treatment. The difference in mass before and after enzyme degradation is indicative of collagen or elastin stability. More loss in mass suggests a decrease in stability.

Figure 1D:
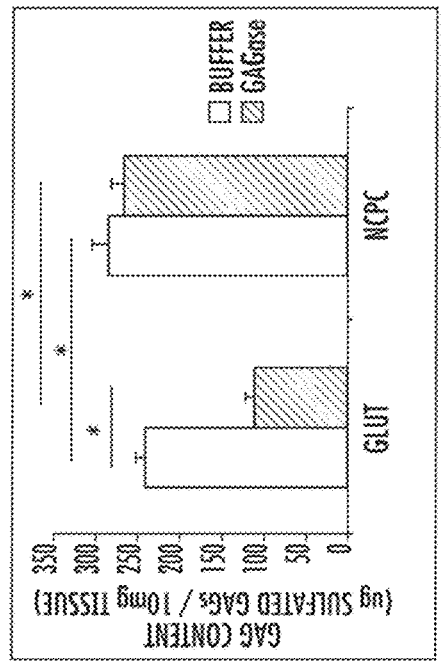
Figure 1A:
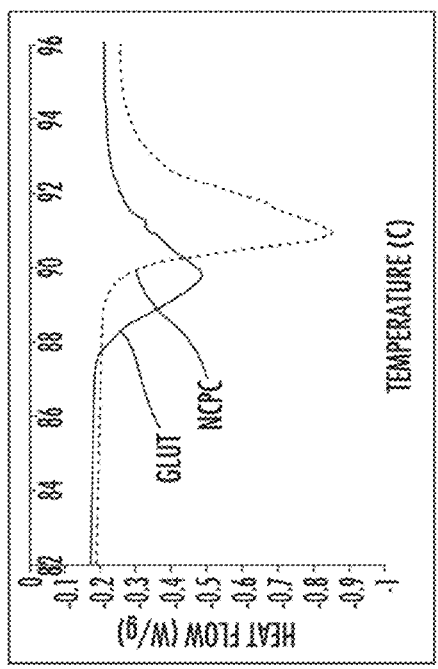

FIG. 1A presents a DSC curve comparing the GLUT and NCPC leaflets. This data is indicative of collagen stability, with a higher denaturing temperature indicating higher stability of the collagen in the tissue. The average denaturing temperature for the GLUT treated materials was 88.1° C., and that for the NCPC treated materials was 90.2° C. As can be seen, the results indicate that the NCPC treatment method provided equivalent or more crosslinking than the GLUT treatment alone.

Figure 1C:
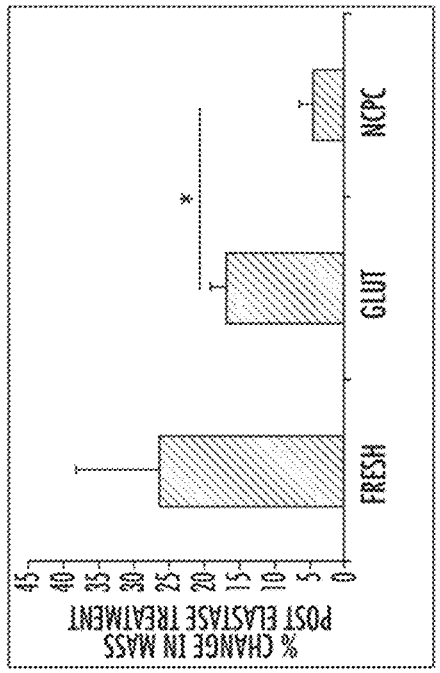

FIG. 1B-1C illustrate the % change in mass following treatment with collagenase (FIG. 1B), elastase (FIG. 1C) and GAGase (FIG. 1D). As noted in the figures, NCPC leaflets demonstrate slightly lower mass loss as GLUT post collagenase treatment and a decreased mass loss compared to GLUT post elastase treatment. This suggests the same or slight increased level of collagen stability in NCPC as GLUT and increased elastin stability in NCPC over GLUT.

GAG stability was assayed by treating either GLUT or NCPC leaflets with a buffer or GAGase (proteolytic enzyme that degrades a variety of GAGs) and detecting the remaining amount of GAGs with a hexosamine assay. By determining GAG retention compared to the buffer (untreated) group in each leaflet group, GAG stability was determined. Hexosamine data in FIG. 1D suggests that NCPC leaflets retained GAGs better between the buffer and GAGase group than GLUT leaflets. FIG. 1D also indicates that NCPC valves retained GAGs better in both the buffer and GAGase group than GLUT valves.

Stability of the treated materials was also determined, with the collagenase, elastase, and GAGase treatments repeated following 21 days, 60 days, and 180 days storage. Results are provided in FIG. 2A (collagenase), FIG. 2B (elastase), and FIG. 2C (GAGase). As can be see, the mass loss following treatment with collagenase was better or about the same in NCPC treated material as for the glutaraldehyde treated materials. The materials maintained their excellent stability when challenged with both elastase and GAGase over the long storage term.

Biomechanical testing was carried out on both the GLUT and NCPC leaflets. Specifically, both GLUT and NCPC valves were subjected to thickness determination, area stretch and biaxial tension testing to characterize the biomechanics of the tissue composite produced from our chemical treatments. As shown, the thickness of the materials was independent of the fixation method (FIG. 3A). The area stretch results indicated that the NCPC treated materials presented significantly different results than the traditionally fixed materials (FIG. 3B). Biaxial testing included radial testing and circumferential testing, as indicated in FIG. 3C. FIG. 3C presents the stress/strain curve for the materials in both directions. As can be seen with reference to FIG. 3C, the leaflets stabilized according to the disclosed stabilization technique are a more compliant biomaterial that may be more suitable for mechanical function in-vivo.

The two fixation methods were also examined qualitatively through histology using various staining methodologies prior to and following implantation. NCPC and GLUT valve material was subjected to histology characterizations pre-implantation. NCPC or GLUT valves were then implanted in juvenile rats subcutaneously for 90 days. Implants were excised and post-implantation samples were subjected to histology characterizations.

Both pre- and post-implantation histology samples were stored in 10% formalin then embedded in paraffin. Embedded samples were then sectioned and stained with Hemotoxyling and Eosin staining (H&E, FIGS. 4A-FIG. 4D), Movat's Pentachrome staining (FIGS. 4E-4H), and Alcian Blue staining. As can be seen with reference to the figures, materials fixed according to traditional GLUT methods exhibit higher calcification (FIGS. 4A-4D), lower levels of elastin (FIGS. 4E-4H), and lower levels of GAG (FIGS. 4I-4L).

Alizarin red staining was also utilized with histology samples pre- and post-implantation to characterize calcification. As shown in FIG. 5A-5D, GLUT fixation methods led to significantly higher calcification deposits post-implantation (FIG. 5B) as compared to NCPC fixations methods (FIG. 5D).

Samples for inductively coupled plasma mass spectrometry analysis (ICP) were digested in 6M HCl for 22 hours and then dried over nitrogen. Samples were then diluted in 2 mL of 0.1 M HCl and analyzed. As indicated in FIG. 5E and FIG. 5F, NCPC samples were found to have significantly less calcium and phosphorus content than GLUT samples which corroborates the histology results. This suggests that NCPC is not as prone to calcification as GLUT.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole and in part. Therefore, the spirit and scope of the appended claims should not be limited to the description of the preferred versions contained therein.

What is claimed is:

1. A method for stabilizing ex vivo or in vitro a cardiac/heart valve connective tissue comprising:
   a first step including contacting the ex vivo or in vitro connective tissue with a neomycin trisulfate salt, the connective tissue including collagen, elastin, and one or more glycosaminoglycans;
   a second step carried out subsequent to the first step, the second step including contacting the ex vivo or in vitro connective tissue with a solution comprising a first carbodiimide crosslinking reagent and pentagalloylglucose;
   a third step carried out subsequent to the second step, the third step including contacting the ex vivo or in vitro connective tissue with a second carbodiimide crosslinking reagent.

2. The method of claim 1, wherein the ex vivo or in vitro connective tissue comprises a heart valve leaflet.

3. The method of claim 1, wherein the neomycin trisulfate salt is provided at a concentration of about 0.2 mM or greater.

4. The method of claim 1, wherein the contact of the first step is carried out for a period of time of about 30 minutes or more.

5. The method of claim 1, wherein the first carbodiimide crosslinking reagent comprises 1-ethyl-3-(3 dimethylaminopropyl) carbodiimide.

6. The method of claim 5, the solution comprising the first carbodiimide crosslinking reagent and pentagalloylglucose further comprising N-hydroxysuccinimide.

7. The method of claim 1, wherein the first carbodiimide crosslinking reagent is provided at a concentration of about 10 millimolar or greater.

8. The method of claim 1, wherein the solution comprises the pentagalloylglucose at a concentration of about 3 millimolar or greater.

9. The method of claim 1, wherein the contact of the second step is carried out for a period of time of about 12 hours or more.

10. The method of claim 1, wherein the second carbodiimide crosslinking reagent is the same as the first carbodiimide crosslinking reagent.

11. The method of claim 1, wherein the second carbodiimide crosslinking reagent comprises 1-ethyl-3-(3 dimethylaminopropyl) carbodiimide.

12. The method of claim 1, wherein the second carbodiimide-crosslinking reagent is provided at a concentration of about 10 millimolar or greater.

13. The method of claim 1, wherein the contact of the third step is carried out for a period of time of about 12 hours or more.

14. A stabilized ex vivo or in vitro connective heart valve tissue comprising a neomycin trisulfate salt and a pentagalloylglucose.

15. The stabilized ex vivo or in vitro connective tissue of claim 14, the tissue having a glycosaminoglycan concentration of greater than about 150 micrograms per 10 milligrams of the tissue.

16. The stabilized connective tissue of claim 14, wherein the tissue is a component of a bioprosthetic implant.

17. The stabilized connective tissue of claim 16, wherein the bioprosthetic implant is a heart component implant.

18. The stabilized connective tissue of claim 17, wherein the heart component implant is a bioprosthetic heart valve.

* * * * *